United States Patent
Koppel et al.

(10) Patent No.: US 6,770,886 B1
(45) Date of Patent: Aug. 3, 2004

(54) DETECTOR-SHIELD ASSEMBLY FOR X-RAY REFLECTOMETRIC SYSTEM

(75) Inventors: Louis N. Koppel, Redwood City, CA (US); Charles Schmelz, Redwood City, CA (US)

(73) Assignee: Therma-Wave, Inc., Fremont, CA (US)

( * ) Notice: Subject to any disclaimer, the term of this patent is extended or adjusted under 35 U.S.C. 154(b) by 443 days.

(21) Appl. No.: 09/969,561

(22) Filed: Oct. 2, 2001

Related U.S. Application Data

(60) Provisional application No. 60/239,282, filed on Oct. 10, 2000.

(51) Int. Cl.[7] .............................................. H01L 31/02
(52) U.S. Cl. ..................... 250/370.14; 378/89
(58) Field of Search ........................ 250/370.14; 378/89

(56) References Cited

U.S. PATENT DOCUMENTS

| | | | |
|---|---|---|---|
| 3,869,615 A | 3/1975 | Hoover et al. | 250/508 |
| 4,096,391 A | 6/1978 | Barnes | 250/505 |
| 4,118,632 A | 10/1978 | Luig | 250/513 |
| 4,286,156 A | 8/1981 | Wagner | 250/363 |
| 4,315,146 A | 2/1982 | Rudin | 250/515 |
| 4,465,540 A | 8/1984 | Albert | 156/252 |
| 4,493,098 A | 1/1985 | Riihimäki et al. | 378/146 |
| 4,609,823 A | 9/1986 | Berger et al. | 250/370 |
| 4,814,620 A | 3/1989 | Comey et al. | 250/352 |
| 5,567,971 A * | 10/1996 | Jackson et al. | 257/431 |
| 5,619,548 A | 4/1997 | Koppel | 378/70 |
| 6,389,102 B2 * | 5/2002 | Mazor et al. | 378/89 |
| 6,453,006 B1 | 9/2002 | Koppel et al. | 378/86 |
| 6,600,160 B2 * | 7/2003 | Kobayashi et al. | 250/370.14 |

FOREIGN PATENT DOCUMENTS

EP            0 281 172            2/1988

* cited by examiner

*Primary Examiner*—Constantine Hannaher
*Assistant Examiner*—Shun Lee
(74) *Attorney, Agent, or Firm*—Stallman & Pollock LLP

(57) ABSTRACT

A detector assembly is introduced that provides shielding of irradiation vulnerable regions of an X-ray detector against directly impinging and scattered X-rays. A shielding unit has a primary aperture to shape an X-ray beam reflected from a test area of a work piece such that the shaped beam directly impinges an X-ray sensing area of the detector. A secondary aperture shields off X-rays scattering off along the edges of the primary aperture. In the preferred embodiment, the shielding unit is a monolithic structure. An area between primary and secondary aperture is laterally recessed to prevent a portion of scattered X-rays from being deflected onto the sensing area.

41 Claims, 4 Drawing Sheets

DETECTOR-SHIELD ASSEMBLY FOR X-RAY REFLECTOMETRIC SYSTEM

PRIORITY CLAIM

The present application claims priority to the U.S. Provisional Patent Application Serial No. 60/239,282 filed Oct. 10, 2000, which is incorporated herein by reference.

CROSS REFERENCE

The present application cross references the disclosures of U.S. Pat. No. 6,453,006 B1, issued Sep. 17, 2002, and U.S. Pat. No. 5,619,548, issued Apr. 8, 1997, which are incorporated herein by reference.

FIELD OF INVENTION

The present invention relates to X-ray reflectometric systems that utilize characteristics of X-rays reflected from a thin film layer to determine structural properties of the thin film layer. Particularly, the present invention relates to detector-shield assemblies for such X-ray reflectometric systems.

BACKGROUND OF THE INVENTION

In X-ray reflectometry of the type described in the above-identified prior art, X-rays are focused onto the surface of a work piece such that X-ray reflections occur in a predetermined angular range. An X-ray detector is positioned in an X-ray reflectometric system such that a relevant portion of the reflected X-rays impinge upon the detector on a sensing area comprising an array of detectors. Each element in the array corresponds to a different angle of incidence of the X-rays in the detector. These elements are resistant to irradiation damage.

In the case where an X-ray detector includes a photodiode array, the primary area is a linear array of X-ray sensitive PN photodiodes, which are well known to those skilled in the art. PN photodiodes suffer little or no degradation when exposed to X-rays. This type of detector also includes an array of readout circuits also denoted as a diode read-out section, which extends preferably parallel to the photodiode array. The read-out circuit performs well-known electronic operations to produce together with the photodiode array an electric signal that corresponds to various characteristics of the impinging X-rays. The read-out circuit includes MOS transistor devices, as they are well known to one skilled in the art. MOS transistors have a leakage characteristic that becomes irreversibly degraded by X-ray exposure. In order to prevent the performance characteristic of an X-ray detector from degrading, this irradiation vulnerable area needs to be shielded against X-rays.

In the prior art and according to FIG. 1, a radiation source 1 provides a focused monochromatic X-ray beam 2 onto a test area 3 of a work piece 12. As is described in the U.S. patent application Ser. No. 09/527,389, filed Mar. 16, 2000, and U.S. Pat. No. 5,619,548, issued Apr. 8, 1997, the beam emitted from the radiation source is typically focused onto the sample by a curved monochometer (not shown). The focused X-ray beam 5 is reflected from the test area 3. A single aperture plate 6 made of radiation opaque material is commonly positioned in the path of the reflected beam 5 in order to limit direct irradiation only to the dedicated sensing area 10 of the detector 8. Unfortunately, the aperture plate 6 creates stray radiation 7 along the plate edges. It is noted that stray radiation 7 is commonly referred to as scattered radiation. With increasing sensitivity of an X-ray detector 8, stray radiation 7 impinging the irradiation vulnerable area 11 (See FIG. 2) becomes a significant factor in the detector's feasible life span. In the case of a photodiode array detector, the dark current characteristic and sensitivity suffer irreversible and detrimental change after about one hour of operational use of the detector.

Therefore, there exists a need for a detector-shield assembly in an X-ray reflectometric system configured to prevent stray radiation from reaching the irradiation vulnerable area of the detector. The present invention addresses this need.

SUMMARY OF THE INVENTION

A detector-shield assembly is introduced that includes at least two apertures positioned and shaped in correspondence to each other, to the sensing area and to the irradiation vulnerable area. A primary aperture is positioned and shaped in correspondence with the reflected X-ray beam and the sensing area. The primary aperture consequently defines the shape of the X-ray beam impinging directly on the sensing area. A secondary aperture is placed between the primary aperture and the detector. The secondary aperture is preferably placed immediately adjacent to the detector.

The apertures may be defined by an opening in a solid plate or by two or more elements suitably positioned to define an opening. For example, a pair of razor blades can be aligned with each other and spaced apart to define an aperture. These structural arrangements, whether a single plate with an opening or separate elements configured to define an opening, will be referred to herein as an "aperture plate" for ease of description. The surface of the aperture plate functions to deflect and/or absorb X-rays striking that surface outside the perimeter of the opening.

The size of the secondary aperture is slightly larger than the primary aperture such that the shaped beam formed by the first aperture may pass without interference through the secondary aperture. Stray radiation scattered or deflected by the primary aperture will be captured by the secondary aperture. Specific dimensioning of the secondary aperture provides for a minimal extension of lateral stray radiation on the detector front. The portion of the lateral stray radiation extension, which is lateral and immediately adjacent to the detector array (impinging area) is called the X-ray half shadow. The secondary aperture functions to reduce this half shadow.

In the preferred embodiment of the present invention both apertures are defined by a single monolithic structure made from a radiation opaque material like, for example, stainless steel or tantalum. Fabricating the apertures as a monolithic structure provides for highest dimensional precision between primary and secondary aperture. The area between the primary and secondary aperture is preferably laterally recessed such that a portion of the emitted stray radiation is laterally dispersed.

DETAILED DESCRIPTION OF THE INVENTION

Figure 1:
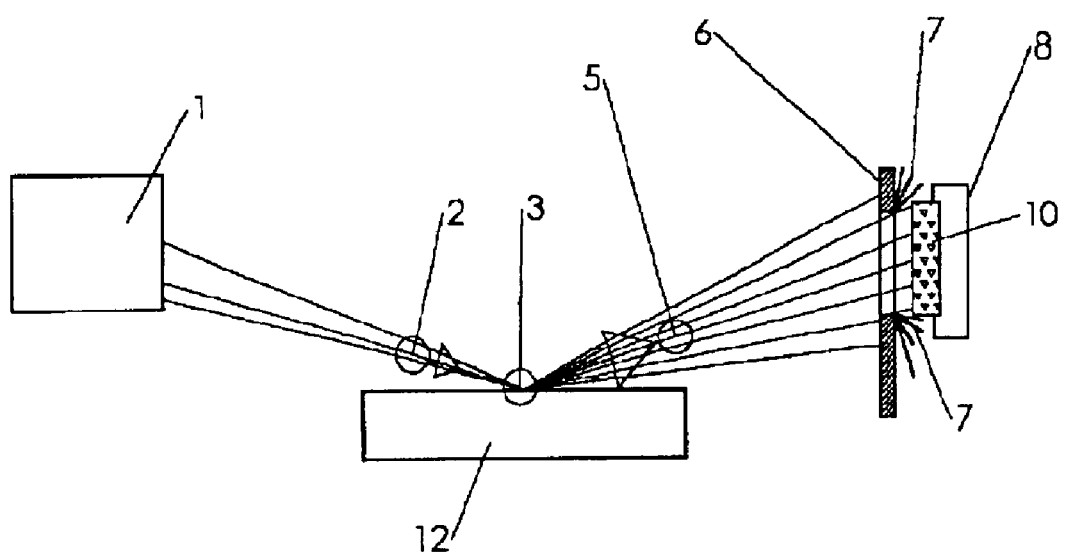
FIG. 1 shows a schematic prior art X-ray reflectometric system having a single aperture shield.
Figure 2:
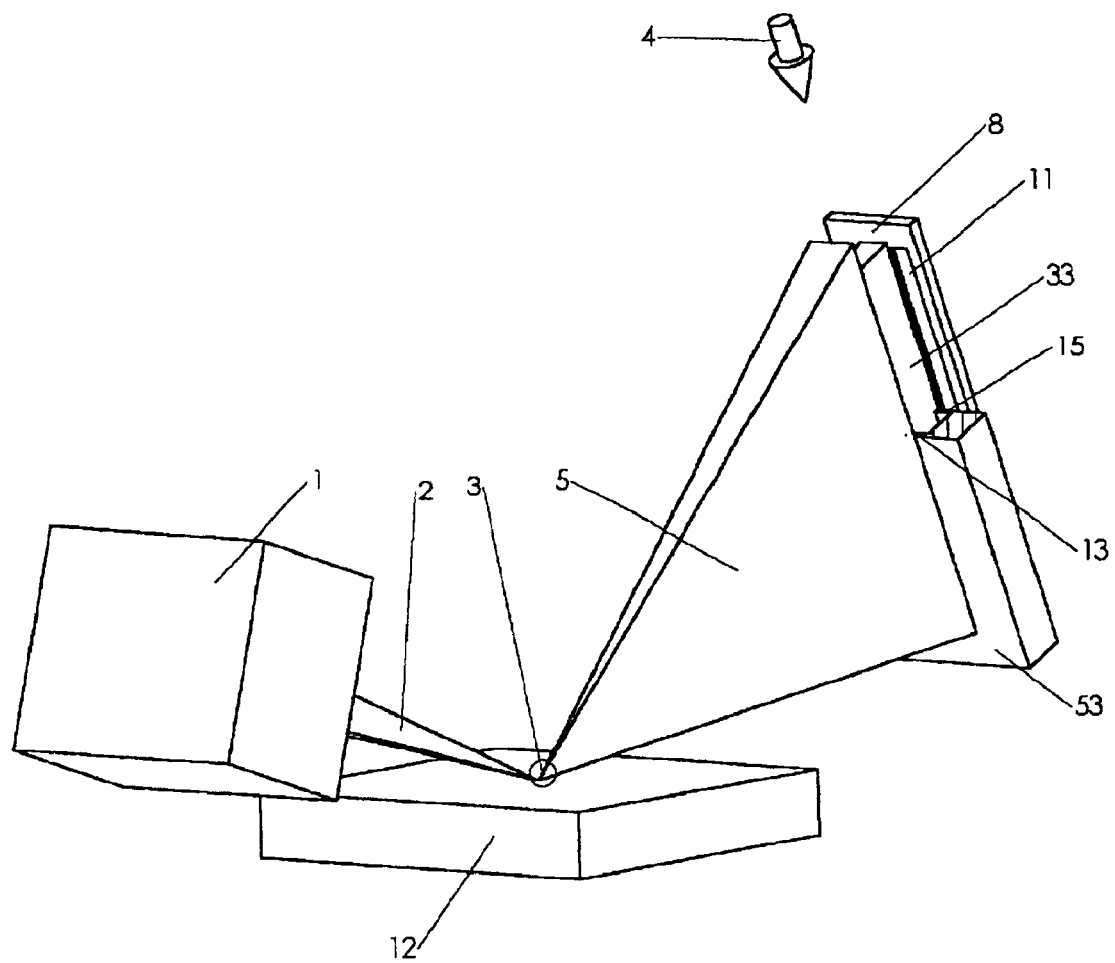
FIG. 2 shows a schematic three dimensional view an X-ray reflectometric system including a detector-shield assembly of the present invention.

An X-ray reflectometric system according to the preferred embodiment of the present invention is schematically illustrated in FIG. 2. Details about the function and operations of such system may be obtained from the disclosures of U.S. patent application Ser. No. 09/527,389, filed Mar. 16, 2000, and U.S. Pat. No. 5,619,548, issued Apr. 8, 1997.

The main components and the basic function of an X-ray reflectometric system are described in the following. FIG. 2 shows a three dimensional view of an exemplary X-ray reflectometric system. A shielding unit 53 is shown in FIG. 2 as being broken up in order to illustrate a portion of a shaped beam 33 and a portion of a detector 8. Hatch lines indicate the break section. A view arrow 4 shows the view direction of FIG. 3. According to FIG. 2, an X-ray source 1 provides a specifically configured and focused X-ray beam 2 onto a dedicated test area 3 of a work piece 12. The focused beam 2 is directed onto the work piece 12 in a fashion that produces a reflected X-ray beam 5 traveling off the test area 3. A primary aperture plate 13 has a primary aperture 30 (see FIG. 3) positioned and shaped to provide a shaped X-ray beam 33 (see also FIG. 3) by blocking a peripheral portion of the reflected beam 5 from traveling any further. The blocked portion impinges on the front surface 27 (see FIG. 3) of the primary aperture plate 13 where it is absorbed and/or deflected away from the detector 8.

The primary aperture 30 is shaped in correspondence with a sensing area 10 (see FIG. 3) of the detector 8 such that the shaped beam 33 directly irradiates the sensing area 10. In the preferred embodiment, the width of the primary aperture 30 is chosen to be less than the width of the sensing area 10 by a degree corresponding to the accuracy with which the aperture can be positioned over the sensing area. This assures that the direct X-ray beam never strikes any part of the detector other than the PN array. In the preferred embodiment, the width of the primary aperture is about 90 percent of the width of the sensing area.

In the preferred embodiment, the sensing area 10 is occupied by an X-ray sensing device like, for example, a PN photodiode. It is noted that the scope of the invention is not limited to a specific type of sensing device as is clear to one skilled in the art. The primary aperture plate 13 has a primary thickness 47 (see FIG. 3) in correspondence with radiation density and an X-ray impermeability of the primary aperture material. Scattered radiation is emitted essentially isotropically, that is, in all directions equally.

The present invention introduces a secondary aperture plate 15, which is placed along the beam path of the shaped beam 33 to block any stray radiation 7 scattered from the edges of primary aperture 30 from striking area 11. The secondary aperture plate 15 is also placed a secondary distance 48 (see FIG. 3) from the detector 8. In the preferred embodiment, the secondary aperture plate 15 snuggly contacts a ceramic header block 45 (see FIGS. 3, 4) in which the detector 8 is fixed. The secondary distance 48 may be defined by a recess depth with which the detector 8 is recessed in the ceramic block 45. In the preferred embodiment, the secondary distance 48 is between 0.2 mm and 0.5 mm and the outside distance 51 (see FIGS. 3, 4) is between 1 mm and 10 mm. The secondary aperture plate 15 has a secondary aperture 31 (see FIG. 3) that is larger than the primary aperture 30 by an offset distance 37 (see FIG. 3).

The offset distance 37 is selected to prevent the secondary aperture 15 from interfering with the shaped beam 33. In the preferred embodiment, the offset distance 37 is between 0.1 mm and 3 mm.

Figure 3:
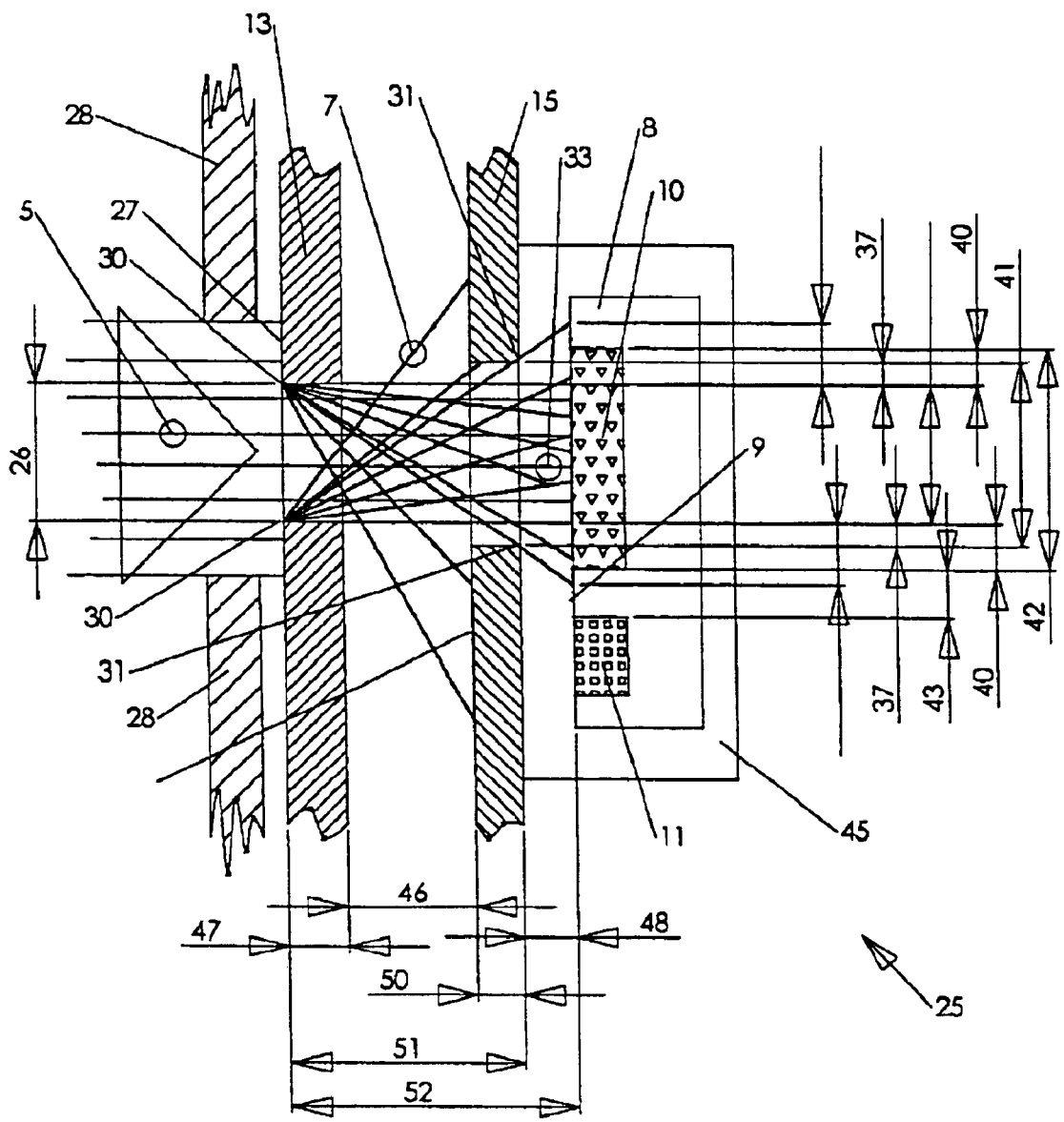
FIG. 3 shows an enlarged schematic section view of an operational detector-shield assembly of the present invention with deflected, shaped and scattered X-rays in a view direction indicated by a arrow 4 of FIG. 2.

According to FIG. 3, the radiation vulnerable area 11 is placed on the detector front 9 together with the sensing area 10. The radiation vulnerable area 11 may be adjacent to the sensing area 10 separated by a lateral distance 43. The lateral distance 43 is preferably kept to a minimum. In the preferred embodiment, the radiation vulnerable area 11 comprises a diode read-out section parallel to one or both sides (see FIG. 4) of the photodiode array occupying the sensing area 10. As is well known to those skilled in the art, the diode readout sections, also denoted as readout circuit, periodically apply a bias voltage to the photodiode array, also denoted as PN photodiode array. In the preferred embodiment, the detector is built with two symmetrically located readout sections, on either side of the diode array. Nevertheless, the scope of the invention includes a case where a single readout section is present on the detector 8. In the preferred embodiment, the lateral distance 43 is less than one millimeter. The apertures 30, 31 are shaped and positioned such that the stray radiation 7 reaching the radiation vulnerable area 11 during operational use of the system is minimized and preferably substantially eliminated. The shaping and positioning of the apertures 30, 31 may also be considered with respect to assembly tolerances between the aperture plates 13, 15 and the photodiode array 10. In a preferred embodiment, the detector 8 is enclosed in a housing, the front cover of which is shown in FIG. 3 as 28 and constrains the spacing between the primary aperture plate 13 and the detector surface.

Figure 4:
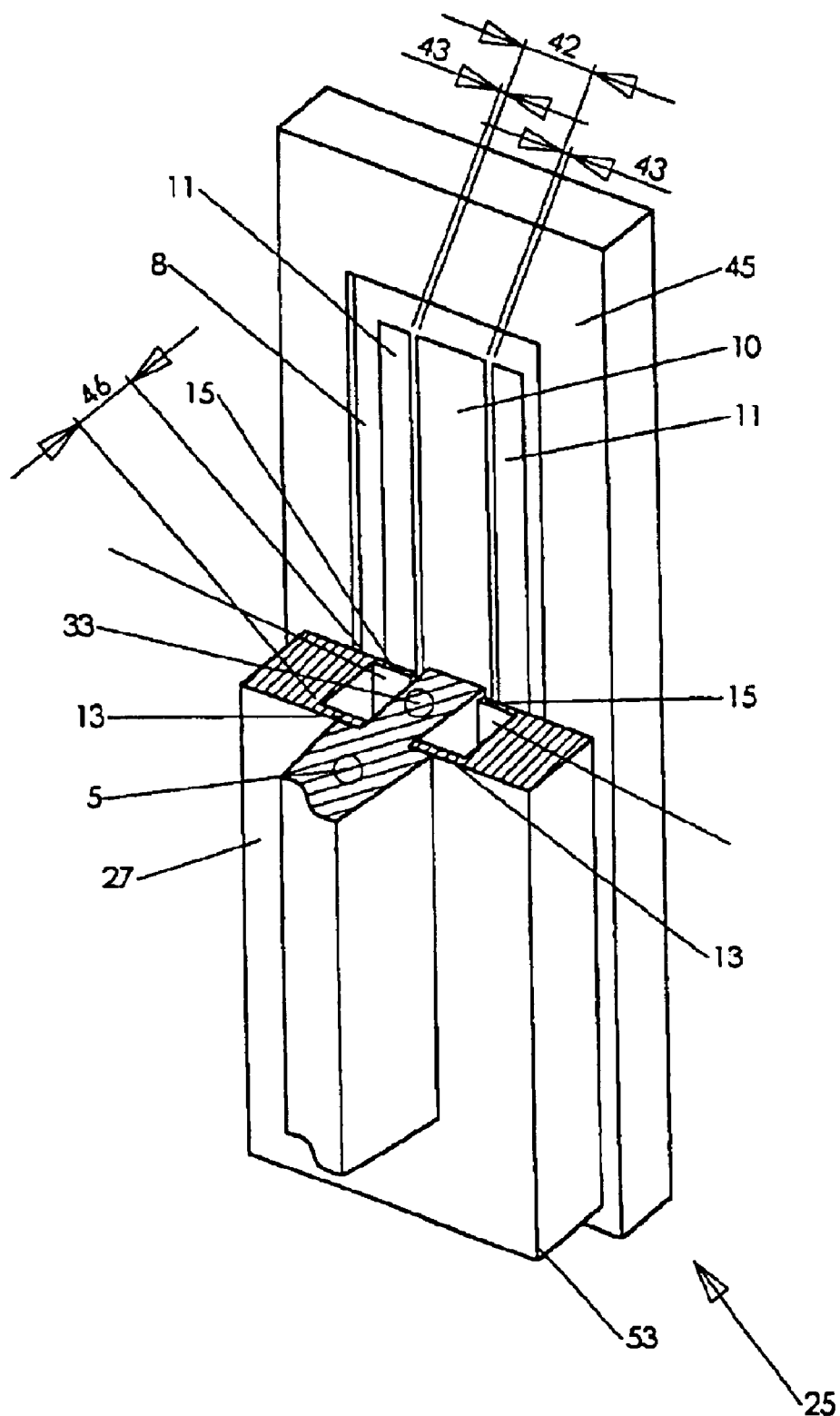
FIG. 4 shows a three dimensional view of an exemplary detector-shield assembly with the shielding unit and a body representation of the impinging X-rays being cut along a vertical symmetry plane.

In FIG. 4, the detector 8 is three-dimensionally illustrated according to a preferred embodiment of the invention. The detector 8 has an elongated shape with the sensing area 10 having the sensing width 42 (see also FIG. 3). Areas 10, 11 extend significantly along the length of the detector. In FIG. 4, the detector 8 is partially hidden by the broken up section of the shielding unit 53 and the broken up solid representation of the reflected beam 5. The detector 8 may be considered to extend in both sides essentially symmetrically and in a fashion as illustrated with the end visible in FIG. 4. Consequently and in accordance to FIG. 4, the lateral distance 43 may be considered mainly in vertical direction. Also, the aperture plates 13, 15 are essentially parallel to the front of the detector 12. Hence, also the apertures 30, 31 may be mainly considered with their primary width 26 (see FIG. 3) and their secondary width 41 (see FIG. 3). Again, considering a symmetric configuration of the apertures relative to the horizontal symmetry plane of the sensing area, the locations of the aperture plates 13, 15 are significant mainly in horizontal direction represented by the primary distance 52 and the secondary distance 48.

Referring back to FIG. 3, for a given outside distance 51 and a given secondary distance 48, the secondary width 41 may be determined as follows. First, the primary width 26 is determined by reducing the given sensing width 42 by twice a compensation extension 40. The compensation extension 40 may be defined in correspondence to assembly and/or fabrication tolerances between the apertures 30, 31 and the detector 8 as they are known to those skilled in the art. After determining the primary width 26, the secondary width 41 may be determined by applying the formula below, in which:

$W_S$ is the secondary width 41,
$W_A$ is the sensing width 42,
$W_R$ is the lateral distance 43,
$W_P$ is the primary width 26, $H_P$ is the primary distance 51

$H_S$ is the secondary distance 48.

$$W_S \leq [H_P/(H_P+H_S)] \cdot (W_R+W_P+\tfrac{1}{2} \cdot W_A) - W_P$$

In order to accomplish the highest possible accuracy of position and shape of the apertures 30, 31 are fabricated in the preferred embodiment from a monolithic structure, which is referred to in FIG. 4 as the shielding unit 53. The fabrication may be accomplished, for example, by milling or electro erosive machining. The preferred materials are stainless steel and or tantalum, since those materials have knowingly a high impermeability to X-rays. Other possible choices include molybdenum, tungsten, and machineable tungsten alloys. Fabricating the primary aperture plate 13 with a primary thickness 47 and fabricating the secondary aperture plate 15 with a secondary thickness 50 may be accomplished on a small scale. Specifically, the primary thickness 47 may be selected to provide an opaque shield against the reflected beam 5. The following table A shows minimal values of the primary thickness 47 either made from stainless steel or from tantalum for a given beam photon energy of the reflected beam 5.

TABLE A

| Aperture material | photon energy | Min primary thickness |
|---|---|---|
| Stainless steel | 0-8 keV | 0.175 mm |
| Tantalum | 8-20 keV | 0.047 mm |

According to Table A, the greater X-ray absorptivity of tantalum manifests itself as a reduced minimum thickness. The secondary thickness 50 may be selected to provide an opaque shield solely against the stray radiation 7. Since the stray radiation 7 has an intensity that is only a fraction of the intensity of the reflected beam 5, the secondary thickness 50 may mainly be selected to comply with requirements for mechanical strength. The secondary aperture plate 15 is also made from X-ray absorptive metal.

The shielding unit 53 further provides a recessed area 46 (see FIGS. 3, 4) between the aperture plates 13, 15. In the recessed area 46 a portion of the stray radiation 7 is laterally dispersed and/or absorbed between the aperture plates 13, 15, rather than being deflected again towards the sensing area 10. Consequently, the amount of total stray radiation 7 impinging the sensing area may be further reduced and the impinging area 10 may be less blurred by stray radiation 7. The detector-shield assembly 25 is preferably assembled by utilizing an alignment feature placed on the shielding unit 53 and the ceramic holder 45 as is clear to one skilled in the art.

The scope of the invention is not limited to any specific configuration of sensing area and/or irradiation vulnerable area. It is clear to one skilled in the art, that the sensing area and/or the irradiation vulnerable area may be configured in numerous ways in order to accomplish varying task within the field of X-ray reflectometry.

The scope of the invention is not limited to a specific configuration of the shielding unit 53. It is clear to one skilled in the art that the shielding unit may have any number of individual parts as may be deemed fit to serve the purpose of the apertures 30, 31 as described in the above. Particularly, the scope of the present invention includes embodiments, in which the apertures 30, 31 are provided by individual plates. Yet in another embodiment, the shielding unit 53 may be formed separately to provide individual adjustment of the aperture plates 30, 31. Further design variations of the shielding unit 53 may be selected in accordance with the teachings above without departing from the scope of the invention.

Accordingly, the scope of the present invention as described in the specification above is set forth by the following claims and their legal equivalent.

What is claimed is:

1. An X-ray detector assembly for an X-ray reflectometric system, said assembly comprising:
   a detector including an X-ray sensing area for receiving an X-ray beam, the detector being configured to produce a signal corresponding to the X-ray beam; and
   a shielding unit including a primary aperture positioned along a beam path of said X-ray beam such that a shaped portion of the X-ray beam impinges on the X-ray sensing area, the shielding unit further including a secondary aperture positioned along the beam path between the primary aperture and the sensing area in order to allow the shaped portion of the X-ray beam to impinge on the X-ray sensing area while minimizing an amount of stray X-rays scattered by the primary aperture from reaching the detector.

2. The assembly of claim 1, wherein said sensing area is a PN photodiode.

3. The assembly of claim 1, wherein the detector further includes a readout circuit located a lateral distance away from said sensing area, and the secondary aperture substantially prevents the stray X-rays from impinging upon the readout circuit.

4. The assembly of claim 3, wherein said readout circuit includes MOS transistor devices.

5. The assembly of claim 3, wherein said lateral distance is less than 1 mm.

6. The assembly of claim 1, wherein said shielding unit is a monolithic structure.

7. The assembly of claim 6, wherein said monolithic structure is made of durable metal having high X-ray absorptivity.

8. The assembly of claim 7, wherein said durable metal is selected from a material group consisting of stainless steel, tantalum, molybdenum, tungsten, and machineable tungsten alloys.

9. The assembly of claim 6, wherein said shielding unit further comprises a recessed area absorbing a portion of said stray X-rays, said recessed area being positioned between said primary aperture and said secondary aperture.

10. The assembly of claim 1, wherein at least one of said primary aperture and said secondary aperture is provided by an aperture plate.

11. The assembly of claim 10, wherein said aperture plate is made of durable metal having high X-ray absorptivity.

12. The assembly of claim 11, wherein said durable metal is selected from a material group consisting of stainless steel, tantalum, molybdenum, tungsten, and machineable tungsten alloys.

13. The assembly of claim 1 further comprising a ceramic holder in which said detector is embedded, said ceramic holder contacting said shielding unit.

14. An X-ray reflectometric system, comprising:
   a planar silicon detector device including a photodiode array configured to receive and sense an X-ray beam, the silicon detector device further including a read-out circuit configured to produce a signal in response to the photodiode array sensing the X-ray beam; and
   a shielding unit including a primary aperture positioned along a beam path of the X-ray beam such that a portion of the X-ray beam is passed to the photodiode array as a shaped beam, the shielding unit further including a secondary aperture positioned along the beam path between the primary aperture and the photodiode array, the secondary aperture having a shape that allows the shaped beam to impinge upon the photodiode array while substantially preventing stray X-rays scattering off the primary aperture from reaching the read-out circuit.

15. The system of claim 14, wherein said shielding unit is a monolithic structure.

16. The system of claim 15, wherein said monolithic structure is made of durable metal having high X-ray absorptivity.

17. The system of claim 16, wherein said durable metal is selected from a material group consisting of stainless steel, tantalum, molybdenum, tungsten, and machineable tungsten alloys.

18. The system of claim 14, wherein said shielding unit further comprises a recessed area absorbing a portion of said scattering X-rays, said recessed area being positioned between said primary aperture and said secondary aperture.

19. The system of claim 14, wherein at least one of said primary aperture and said secondary aperture is provided by an aperture plate.

20. The system of claim 19, wherein said aperture plate is made of durable metal having high X-ray absorptivity.

21. The system of claim 20, wherein said durable metal is selected from a material group consisting of stainless steel, tantalum, molybdenum, tungsten, and machineable tungsten alloys.

22. The system of claim 14, wherein said photodiode array is separated from said read-out circuit by a lateral distance of less than 1 mm.

23. The system of claim 14, further comprising a ceramic holder in which said detector is embedded, said ceramic holder contacting said shielding unit, and wherein a secondary distance between the secondary aperture and the photodiode array corresponds to a recess depth of said detector front within said ceramic holder.

24. A detector shield assembly for an X-ray detector, said X-ray detector having an array of photodetectors for receiving X-rays and an array of electronic elements electrically connected to said photodetectors for generating output signals in response to a detection of X-rays, said array of electronic elements being located adjacent to and spaced from said array of photodetectors, said shield comprising:
 a primary aperture aligned with the photodetector array for passing a portion of an X-ray beam, said primary aperture being dimensioned so that the portion of the beam directly transmitted by the primary aperture has a shape substantially corresponding to the detector array; and
 a secondary aperture disposed between the detector and the primary aperture and aligned with the primary aperture, with the dimensions of the secondary aperture being configured to transmit the portion of the beam transmitted by the primary aperture while minimizing an amount of stray X-rays striking the array of electronic elements, the stray X-rays being scattered by the primary aperture.

25. The assembly of claim 24, wherein said shield assembly is a monolithic structure.

26. The assembly of claim 25, wherein said monolithic structure is made of durable metal having high X-ray absorptivity.

27. The assembly of claim 26, wherein said durable metal is selected from a material group consisting of stainless steel, tantalum, molybdenum, tungsten, and machineable tungsten alloys.

28. The assembly of claim 24, wherein said shield assembly further comprises a recessed area absorbing a portion of said scattering X-rays, said recessed area being positioned between said primary aperture and said secondary aperture.

29. The assembly of claim 24, wherein at least one of said primary aperture and said secondary aperture is provided by an aperture plate.

30. The assembly of claim 29, wherein said aperture plate is made of durable metal having high X-ray absorptivity.

31. The assembly of claim 30, wherein said durable metal is selected from a material group consisting of stainless steel, tantalum, molybdenum, tungsten, and machineable tungsten alloys.

32. The assembly of claim 24, further comprising a ceramic holder in which said detector is embedded, said ceramic holder contacting said shield assembly.

33. The assembly of claim 24 wherein the width of the primary aperture is narrower than the width of the array of photodetectors.

34. The assembly of claim 24 wherein the width of the secondary aperture is greater than the width of the primary aperture.

35. A detector shield assembly for an X-ray reflectometric system, said assembly having an array of photodetectors for receiving X-rays and an array of electronic elements electrically connected to said photodetectors for generating output signals in response to a detection of X-rays, said array of electronic elements being offset less than 1 mm from said array of photodetectors, said shield assembly comprising:
 a primary aperture aligned with the photodetector array for passing a portion of an X-ray beam, said primary aperture having a primary width of about 90 percent of a sensing width of the photodetector array and being located a distance from the photodetector array of between 1.2 mm and 10.5 mm;
 a secondary aperture disposed between the primary aperture and the photodetector array, at a distance between 0.2 mm and 0.5 mm from the photodetector array, the secondary aperture having a secondary width extending between 0.1 and 3 mm beyond the primary width in order to allow passage of the portion of the X-ray beam while minimizing the passage of stray X-rays scattered by the primary aperture.

36. The detector shield assembly of claim 35, wherein said primary aperture is provided by a primary aperture plate.

37. The detector shield assembly of claim 36, wherein said reflectometric system provides said X-rays with a beam photon energy of up to 8 keV and wherein said primary aperture plate is made from stainless steel and comprises a minimum primary thickness of 0.175 mm.

38. The detector shield assembly of claim 36, wherein said reflectometric system provides said X-rays with a beam photon energy of up to 20 keV and wherein said primary aperture plate is made from tantalum and comprises a minimum primary thickness of 0.047 mm.

39. The detector shield assembly of claim 35, wherein said shield assembly has an outside distance between opposing sides of the primary and secondary apertures of between 1 mm and 10 mm.

40. The detector shield assembly of claim 39, wherein said shield assembly is a monolithic structure made from a durable metal having high X-ray absorptivity.

41. The assembly of claim 40, wherein said durable metal is selected from a material group consisting of stainless steel, tantalum, molybdenum, tungsten, and machineable tungsten alloys.

* * * * *